US010927064B2

(12) United States Patent
Van Campenhout et al.

(10) Patent No.: US 10,927,064 B2
(45) Date of Patent: Feb. 23, 2021

(54) PROCESS FOR THE MANUFACTURING OF A COMPOUND COMPRISING A (METH)ACRYLOYL GROUP

(71) Applicant: 3M INNOVATIVE PROPERTIES COMPANY, St. Paul, MN (US)

(72) Inventors: Rudy W. Van Campenhout, Hoboken (BE); Rudolf J. Dams, Antwerp (BE); Eike H. Klunker, Kaarst (DE); Matthias Conradi, Hemsloh (DE); Siegfried R. Goeb, Willich (DE)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 16/766,909

(22) PCT Filed: Dec. 12, 2018

(86) PCT No.: PCT/IB2018/059955
§ 371 (c)(1),
(2) Date: May 26, 2020

(87) PCT Pub. No.: WO2019/123125
PCT Pub. Date: Jun. 27, 2019

(65) Prior Publication Data
US 2020/0369590 A1    Nov. 26, 2020

(30) Foreign Application Priority Data

Dec. 20, 2017 (EP) ..................... 17208987

(51) Int. Cl.
*C07C 67/14* (2006.01)
*C07C 231/02* (2006.01)
*C07C 69/54* (2006.01)
*C07C 233/09* (2006.01)
*B29C 48/405* (2019.01)

(52) U.S. Cl.
CPC ............ *C07C 67/14* (2013.01); *B29C 48/405* (2019.02); *C07C 231/02* (2013.01); *C07C 69/54* (2013.01); *C07C 233/09* (2013.01)

(58) Field of Classification Search
None
See application file for complete search history.

(56) References Cited

U.S. PATENT DOCUMENTS

| 2,013,988 | A | 9/1935 | Meder |
| 4,096,182 | A | 6/1978 | Rupp |
| 2010/0185013 | A1 | 7/2010 | Pinnow |
| 2011/0071307 | A1 | 3/2011 | Ishiyama |
| 2011/0087041 | A1 | 4/2011 | Ishiyama |
| 2017/0120499 | A1 | 5/2017 | Li |

FOREIGN PATENT DOCUMENTS

| EP | 1600276 | 7/2008 |
| JP | S63-063636 | 3/1988 |
| JP | H11-199540 | 7/1999 |
| JP | 2003-026630 | 1/2003 |
| WO | WO 2005-092842 | 10/2005 |
| WO | WO 2009-005937 | 1/2009 |
| WO | WO 2017-147040 | 8/2017 |
| WO | WO 2019-123126 | 6/2019 |
| WO | WO 2019-123127 | 6/2019 |

OTHER PUBLICATIONS

Chevalier, Micro Reactors for Industrial Multiphase Applications: Test Reactions to Develop Innovative Glass Microstructure Designs, Chimica Oggi Chemistry Today, Mar.-Apr. 2008, vol. 26, No. 2, pp. 38-42.
Cvetovich, Formation of Acrylanilides, Acrylamides, and Amides Directly from Carboxylic Acids Using Thionyl Chloride in Dimethylacetamide in the Absence of Bases Organic Process Research & Development, 2006, vol. 10, No. 5, pp. 944-946.
Imai, "Studies on Alkyl Ketene Dimers. VI," Journal of Japan Oil Chemists' Society, vol. 10, No. 7, Jan. 1, 1961, pp. 435-440. XP055484965.
Krtschil, "Cost Analysis of a Commercial Manufacturing Process of a Fine Chemical Compound Using Micro Process Engineering," CHIMIA International Journal for Chemistry 2006, vol. 60, No. 9, pp. 611-617.
Movsisyan, "Safe, Selective, and High-Yielding Synthesis of Acryloyl Chloride in a Continuous-Flow System," ChemSusChem, 2016, vol. 9, No. 15, pp. 1945-1952.
Movsisyan, "Taming Hazardous Chemistry by Continuous Flow Technology", Chemical Society Reviews, 2016, vol. 45, No. 18, pp. 4892-4928.
Schaber "Economic Analysis of Integrated Continuous and Batch Pharmaceutical Manufacturing: A Case Study," Industrial & Engineering Chemistry Research, 2011, vol. 50, No. 17, pp. 10083-10092.
Stempel, The Preparation of Acrylyl Chloride, Journal of American Chemical Society,1950, vol. 72, p. 2299-2300.
Wiles, "Recent Advances in Micro Reaction Technology," Chemical Communications, 2011, vol. 47, pp. 6512-6535.

(Continued)

*Primary Examiner* — Amy C Bonaparte
(74) *Attorney, Agent, or Firm* — Carolyn A. Fischer

(57) ABSTRACT

The present disclosure relates to a process for the manufacturing of a compound comprising a (meth)acryloyl group, wherein the process comprises the steps of: a) providing a multi-screw extruder comprising a reaction chamber; b) providing reactants and reagents comprising: i. an alcohol or a primary or secondary amine; ii. a base; and iii. a (meth)acryloyl halide or a 3-halopropionyl halide; and c) incorporating the reactants and reagents into the reaction chamber of the multi-screw extruder, thereby forming a reaction product stream comprising the compound comprising a (meth)acryloyl group.

15 Claims, No Drawings

(56) References Cited

OTHER PUBLICATIONS

Extended EP Search Report for EP Application No. 17208948.4, dated Jun. 28, 2018, 7 pages.
Extended EP Search Report for EP Application No. 17208982.3, dated May 22, 2018, 5 pages.
Extended EP Search Report for EP Application No. 17208987.2, dated May 23, 2018, 6 pages.
International Search Report for PCT International Application No. PCT/IB2018/059957, dated Apr. 9, 2019, 5 pages.
International Search Report for PCT International Application No. PCT/IB2018/059956, dated Feb. 12, 2019, 4 pages.
International Search Report for PCT International Application No. PCT/IB2018/059955, dated Feb. 5, 2019, 4 pages.

PROCESS FOR THE MANUFACTURING OF A COMPOUND COMPRISING A (METH)ACRYLOYL GROUP

CROSS REFERENCE TO RELATED APPLICATIONS

This application is a national stage filing under 35 U.S.C. 371 of PCT/IB2018/059955, filed Dec. 12, 2018, which claims the benefit of European Application No. 17208987.2, filed Dec. 20, 2017, the disclosure of which is incorporated by reference in its/their entirety herein.

RELATED APPLICATIONS

This application claims the benefit of EP Application No. EP17208987.2, filed Dec. 20, 2017, the disclosure of which is incorporated by reference in its entirety herein.

TECHNICAL FIELD

The present disclosure relates to the field of manufacturing compounds comprising a (meth)acryloyl group, in particular to a process using a multi-screw extruder.

BACKGROUND

Compounds comprising a (meth)acryloyl group, such as (meth)acrylic esters and (meth)acrylic amides, have a variety of uses, such as monomers or co-monomers for making a variety of polymers. These compounds can be produced industrially, such as by esterification or amidification of an alcohol or an amine with an (meth)acryloyl chloride in the presence of a base which is intended to neutralize the hydrogen chloride formed during the reaction. This method is not fully satisfactory for the manufacture of all compounds comprising a (meth)acryloyl group, since this method requires the use of solvent often resulting in the formation of highly viscous, pasty or solid intermediate mixtures, which therefore require additional processing steps or could lead to disruption of the production line. Moreover, these known methods can be difficult to perform on an industrial scale because it is necessary to rigorously exclude water from the reaction in order to proceed in high yield. Also, because the reaction is highly exothermic, it is required to proceed both with very slow addition of the alcohol or the amine to the (meth)acryloyl chloride and effective cooling. Even if appropriate cooling steps are performed, the reaction can still pose a risk of fire or explosion when performed on an industrial scale. Furthermore, due to the slow addition of the (meth)acryloyl chloride required in the known method, the conversion of alcohol or amine is gradually performed during the process, which often leads to the formation of unwanted side-products such as for example Michael adducts between residual alcohol or amine and the compound comprising a (meth)acryloyl group.

Partial solutions are described in WO2017/147040 (Dams et al.), U.S. Patent Application Publication No. 2011/0071307 A1 (Ishiyama et al.) and U.S. Patent Application Publication No. 2011/0087041 A1 (Ishiyama et al.), which disclose the manufacturing of (meth)acrylates using the so-called micro reactor technology, also known as flow technology. The disclosed methods are not fully satisfactory for the manufacturing of (meth)acrylic esters or (meth)acrylic amides since they require using solvents and since the viscous, pasty or even solid starting materials or intermediate mixtures formed during the process often lead to blocking of the reactors, especially after prolonged reaction times.

Without contesting the technical advantages associated with the manufacturing processes known in the art, there is still a need for a process for the manufacturing of compounds comprising a (meth)acryloyl group, in particular (meth)acrylic esters and (meth)acrylic amides, which overcomes the above deficiencies.

Other advantages of the process of the disclosure will be apparent from the following description.

SUMMARY

According to one aspect, the present disclosure relates to a process for the manufacturing of a compound comprising a (meth)acryloyl group, wherein the process comprises the steps of:
a) providing a multi-screw extruder comprising a reaction chamber;
b) providing reactants and reagents comprising:
   i. an alcohol or a primary or secondary amine;
   ii. a base; and
   iii. a (meth)acryloyl halide or a 3-halopropionyl halide; and
c) incorporating the reactants and reagents into the reaction chamber of the multi-screw extruder, thereby forming a reaction product stream comprising the compound comprising a (meth)acryloyl group.

In another aspect, the present disclosure is directed to the use of a multi-screw extruder for the manufacturing of a compound comprising a (meth)acryloyl group and which has a weight average molecular weight of less than 1,000 g/mol.

DETAILED DESCRIPTION

According to one aspect, the present disclosure relates to a process for the manufacturing of a compound comprising a (meth)acryloyl group, wherein the process comprises the steps of:
a) providing a multi-screw extruder comprising a reaction chamber;
b) providing reactants and reagents comprising:
   i. an alcohol or a primary or secondary amine;
   ii. a base; and
   iii. a (meth)acryloyl halide or a 3-halopropionyl halide; and
c) incorporating the reactants and reagents into the reaction chamber of the multi-screw extruder, thereby forming a reaction product stream comprising the compound comprising a (meth)acryloyl group.

In the context of the present disclosure, it has been surprisingly found that a process as described above provides an efficient, simple, safe and versatile method for the manufacturing of compounds comprising a (meth)acryloyl group, in particular (meth)acrylic esters and (meth)acrylic amides, wherein the process is in particular also suitable for the manufacturing of compounds comprising a (meth)acryloyl group which involve processing highly viscous, pasty or even solid intermediate mixtures (formed during the reaction process) or starting materials.

In some beneficial aspects, the process as described above is a robust and production-efficient process, which can be performed in the absence of any solvent. The process of the present disclosure further provides excellent control of the reaction temperature profile (efficient thermal management), in particular through ensuring rapid and homogeneous mixing, as well as rapid and efficient transport of the starting material and intermediate reaction mixtures during the reaction process. As such, the process of the present disclosure allows using a broad scope of possible starting material and reagents for the manufacturing of compounds comprising a (meth)acryloyl group without the need of cooling steps.

In some other advantageous aspects, the process as described above is able to provide high yield of reactive (e.g. polymerizable) compounds having excellent purity and quality due to the suppression or substantial reduction of side reactions caused by poor mixing or ageing in conventional batch reactors and other known processes.

In a further advantageous aspect of the process, the contact of reactants with air and/or moisture may be excluded and exposure of the reactants to workers minimized, due to the multi-screw extruder extruder operating in a closed environment.

In still a further beneficial aspect, the process of the disclosure may be performed in the presence of a diluent, in particular diluent monomers such as e.g. (meth)acrylate monomers.

Without wishing to be bound by theory, it is believed that these excellent properties are due in particular to the specific use of a multi-screw extruder comprising a reaction chamber. Surprisingly, the process of the disclosure involves usage of a multi-screw extruder for the manufacturing of compounds comprising a (meth)acryloyl group and being still reactive, in particular being still polymerizable. As exemplified in "*Extrusion of Polymers: Theory and Practice*, Chan I. Chung K. Kim, Carl Hanser Verlag, Munich 2000", in U.S. Patent Application Publication No. 2017/0120499 A1 (Li) or in EP-A1-1 600 276 (Ek et al.), multi-screw extruders are typically used for manufacturing polymeric materials, such as polyurethanes, and not reactive monomers or co-monomers, let alone monomers comprising a (meth)acryloyl group.

Surprisingly, the technical challenge of manufacturing compounds comprising a reactive (meth)acryloyl group, in particular polymerizable (meth)acrylic esters and (meth) acrylic amides monomers in a multi-screw extruder has been realized without or with minimal amounts of polymerization inhibitors.

The term "alkyl" means a linear or branched, cyclic or acyclic, saturated monovalent hydrocarbon radical. Alkyl radicals can have any number of carbon atoms; the number of carbon atoms is often denoted in this disclosure by the notation "Cn" wherein "n" is an integer that corresponds to the number of carbon atoms. Thus, C1 means one carbon atom, C2 means two carbon atoms, C3 means 3 carbon atoms, etc. Typical alkyl groups are C30 or less, such as C26 or less, C24 or less, C22 or less, C20 or less, C18 or less, C16 or less, C12 or less C10 or less, C9 or less, C8 or less, C7 or less, C6 or less, C5 or less, C4 or less, C3 or less, or C2 or less. Many alkyl groups are C1 or greater, C2 or greater, C3 or greater C4 or greater, C5 or greater, C6 or greater, C7 or greater, C8 or greater, C9 or greater C10 or greater, C12 or greater, C14 or greater, C16 or greater, C18 or greater, C20 or greater, C22 or greater, C24 or greater, C26 or greater, or C28 or greater. Other alkyl radicals are also possible. Particular alkyl radicals are methyl.

In the context of the present disclosure, the term "compound comprising a (meth)acryloyl group" is meant to refer to (meth)acrylic esters and (meth)acrylic amides, wherein (meth)acrylic esters refer to esters of acrylic acid or methacrylic acid (also referred to as 2-methylacrylic acid), and (meth)acrylic amides refer to amides of acrylic acid or methacrylic acid.

The term "(meth)acryloyl halide" is meant to refer to acryloyl chloride and methacryloyl chloride (also referred to as 2-methylacryloyl chloride), acryloyl bromide and methacryloyl bromide.

The term "3-halopropionyl halide" is meant to refer to a propionyl halide bearing a halide radical that is covalently bonded to a carbon atom in the 3-position, i.e., the carbon atom in the beta position with respect to the carbonyl. Typically, the term is meant to refer to 3-chloropropionylchloride or 3-bromopropionylbromide.

In the context of the present disclosure, the term "addition stream" is meant to refer to reactants and reagents (such as e.g. the alcohol, the primary or secondary amine, the (meth)acryloyl halide or 3-halopropionyl halide) flowing from an entry location to the reaction chamber of the multi-screw extruder.

The term "reaction chamber" is meant to refer to a closed region or area of the multi-screw extruder, comprising the multiple screws and where separate incoming addition streams are combined and contact one another. The reactants of the addition streams mix and chemically react with one another thereby forming a reaction product stream, where one or the other of the reactants may surround the other. The reaction chamber may contain several segments, each operating at the same or different working conditions, such as mixing and conveying regimes. Each segment may provide suitable addition ports for the various addition streams.

In the context of the present disclosure, the term "flow speed" is meant to refer to the speed (in ml/min) at which an addition stream is incorporated into the reaction chamber of the multi-screw extruder.

The term "residence time" is meant to refer to the period of time the reaction product stream remains in the reaction chamber of the multi-screw extruder from the moment the reactants and reagents, and in particular the first addition stream, the second addition stream and the optional third addition stream are incorporated and mixed into the reaction chamber of the multi-screw extruder until the moment the reaction product stream exits the reaction chamber.

In the context of the present disclosure, the expression "equivalent ratio of compound X to compound Y" is meant to refer to the ratio of the equivalents of compounds X and Y used in the corresponding reaction. The calculation of the equivalent ratio of two compounds is well within the capabilities of those skilled in the art.

In the context of the present disclosure still, the expression "conversion rate of the (meth)acryloyl halide or the 3-halopropionyl halide into the compound comprising a (meth)acryloyl group" is meant to refer to the molar percentage of either (meth)acryloyl halide or the 3-halopropionyl halide which is actually converted into the compound comprising a (meth)acryloyl group, as determined by $^1$H NMR spectroscopy on the unpurified reaction mixture.

The process of the present disclosure comprises, as a first technical feature, the step of providing a multi-screw extruder comprising a reaction chamber.

Multi-screw extruders for use herein are not particularly limited. Any multi-screw extruder comprising a reaction chamber commonly known in the art may be used in the context of the present disclosure. Suitable multi-screw extruders for use herein will be easily identified by those skilled in the art, in the light of the present description.

Moreover, twin screw extrusion methods and devices have been well catalogued in recent publications such as in "Twin Screw Extrusion: Technology and Principles (2$^{nd}$ Ed.), James L. White and Eung K. Kim, Carl Hanser Verlag, Munich 2010", in "Co-rotating Twin-Screw Extruders: Fundamentals, Technology and Applications, Klemens Kohlgruber and Werner Wiedmann, Hanser, Munich 2008" or in "Reactive Extrusion: Principles and Applications, Günter Beyer and Christian Hopmann, Wiley-VCH, Weinheim 2017". One suitable multi-screw extruder is commercially available, for example, under the trade designation PROCESS 11 PARALLEL TWIN-SCREW EXTRUDER (Thermo Fischer Scientific, Germany).

In a particular aspect of the present disclosure, the multi-screw extruder for use herein is selected from the group of twin-screw extruders, planetary roller extruders, and ring extruders. In that respect, the multi-screw extruder for use herein may be a co-rotating multi-screw extruder or a counter-rotating multi-screw extruder.

In one preferred aspect, the multi-screw extruder for use in the process according to the disclosure is a twin-screw extruder, in particular a co-rotating twin-screw extruder.

In an alternative execution, the multi-screw extruder for use herein is a planetary roller extruder comprising in particular a center spindle and multiple planetary gear spindles with center spindle and planetary gear spindles featuring a screw like geometry.

Selecting and fine-tuning the various operating parameters of the multi-screw extruder to the specifics of the targeted chemical reaction, is well within the capabilities of those skilled in the art. These operating parameters will be typically adapted in particular to the nature of the starting material and the targeted compound comprising a (meth) acryloyl group.

In one exemplary aspect, the multi-screw extruder is operated at a screw speed in a range from 10 to 1200 rpm, from 20 to 1000 rpm, from 30 to 800 rpm, from 50 to 800 rpm, from 50 to 600 rpm, from 80 to 600 rpm, from 100 to 500 rpm, from 150 to 450 rpm, from 180 to 400 rpm, from 180 to 380 rpm, or even from 200 to 350 rpm.

In one particular aspect, the process of the present disclosure further comprises the steps of:
a) providing a first addition stream comprising the alcohol or the primary or secondary amine and the base;
b) providing a second addition stream comprising the (meth)acryloyl halide or the 3-halopropionyl halide; and
c) incorporating the first addition stream and the second addition stream into the reaction chamber of the multi-screw extruder, thereby forming a reaction product stream comprising the compound comprising a (meth) acryloyl group.

In another particular aspect, the process of the present disclosure comprises the steps of:
a) providing a first addition stream comprising the alcohol or the primary or secondary amine;
b) providing a second addition stream comprising (meth) acryloyl halide or the 3-halopropionyl halide;
c) providing a third addition stream comprising the base; and
d) incorporating the first addition stream, the second addition stream and the third addition stream into the reaction chamber of the multi-screw extruder, thereby forming a reaction product stream comprising the compound comprising a (meth)acryloyl group.

As will be easily apparent to those skilled in the art, the multi-screw extruder for use herein may comprise various addition ports for the incorporation of various reactant/ reagent addition streams into the reaction chamber. The various reactant/reagent addition streams may be incorporated into the reaction chamber through distinct or common addition ports. Similarly, the various reactant/reagent addition streams may be incorporated into the reaction chamber simultaneously or at distinct addition times. Similarly, the various reactant/reagent addition streams may be incorporated into the reaction chamber at equal or dissimilar flow speeds.

In an exemplary aspect, the multi-screw extruder further comprises at least a first addition port, a second addition port, and optionally a third addition port, and the first addition stream is incorporated into the reaction chamber of the multi-screw extruder through the first addition port, the second addition stream is incorporated through the second addition port, and the optional third addition stream is incorporated through the optional third addition port.

According to a typical aspect of the process of the present disclosure, the reactants and reagents, and in particular the first addition stream, the second addition stream, and the optional third addition stream are incorporated simultaneously, optionally at a different flow speed, into the reaction chamber of the multi-screw extruder. Alternatively, the reactants and reagents, and in particular the first addition stream, the second addition stream, and the optional third addition stream are incorporated into the reaction chamber of the multi-screw extruder in successive steps.

In practice, the various reactants and reagents, and in particular the various addition streams are incorporated and are allowed to combine and contact one another so as to chemically react with one another in the reaction chamber of the multi-screw extruder, thereby forming a reaction product stream comprising the compound comprising a (meth)acryloyl group.

In one exemplary aspect of the process according to the disclosure, the reactants and reagents, and in particular the first addition stream, the second addition stream, and the optional third addition stream are incorporated and combined, in particular through the movement of the multiple screws, in the reaction chamber of the multi-screw extruder, thereby forming a reaction product stream comprising the compound comprising a (meth)acryloyl group.

The temperature of the various reactants and reagents, and in particular the various addition streams and the temperature of the reaction chamber for use herein are not particularly limited, which is a further advantage of this process and makes the process simple and versatile to operate. Suitable temperatures for use herein will be easily identified by those skilled in the art, in the light of the present description.

In an advantageous aspect of the process, the temperature of the reactants and reagents, and in particular the first addition stream, the second addition stream and the optional third addition stream are such that the reactants and reagents, and in particular the first, second and optionally third addition stream are liquid prior to incorporation into the reaction chamber of the multi-screw extruder. In an alternative aspect, the temperature of the reactants and reagents, and in particular the first addition stream, the second addition stream and the optional third addition stream are such that the reactants and reagents, and in particular the first addition stream, the second addition stream and the optional third addition stream are at least flowable/pumpable through conventional multi-screw extruders addition pumps prior to incorporation into the reaction chamber of the multi-screw extruder.

According to a typical aspect of the process of the present disclosure, the temperature of the reactants and reagents, and in particular the first addition stream, the second addition stream and the optional third addition stream is in a range from 0° C. to 120° C., from 0° C. to 100° C., from 0° C. to 80° C., from 0° C. to 70° C., from 5° C. to 60° C., from 10° C. to 55° C., from 15° C. to 45° C., from 20° C. to 35° C., or even from 20° C. to 25° C., prior to incorporation into the reaction chamber of the multi-screw extruder.

In an advantageous aspect, the temperature of the reactants and reagents, and in particular the first addition stream, the second addition stream and the optional third addition stream is room temperature.

According to another typical aspect of the process, the temperature of the reaction chamber is in a range from 0° C. to 120° C., from 0° C. to 100° C., from 0° C. to 80° C., from 0° C. to 70° C., from 5° C. to 60° C., from 10° C. to 60° C., from 15° C. to 60° C., from 15° C. to 55° C., from 15° C. to 50° C., from 15° C. to 40° C., or even from 20° C. to 30° C., after incorporation of the reactants and reagents, and in particular the first addition stream, the second addition stream and the optional third addition stream.

In still a further typical aspect, the temperature of the reaction chamber is no greater than 120° C., no greater than 100° C., no greater than 80° C., no greater than 60° C., no greater than 50° C., no greater than 40° C., or even no greater than 30° C., after incorporation of the reactants and reagents, and in particular the first addition stream, the second addition stream and the optional third addition stream.

The reactants and reagents, and in particular the various addition streams may be incorporated into the reaction chamber of the multi-screw extruder using any means commonly known in the art. In a particular aspect, the reactants and reagents, and in particular the first addition stream, the second addition stream and the optional third addition stream are incorporated into the reaction chamber by using suitable (high) pressure pumps.

The flow speed of the reactants and reagents, and in particular the various addition streams for use herein is not particularly limited. Suitable flow speeds for use herein will be easily identified by those skilled in the art, in the light of the present description.

In an advantageous aspect of the process, the reactants and reagents, and in particular the first addition stream, the second addition stream and the optional third addition stream are incorporated into the reaction chamber of the multi-screw extruder each at a flow speed in a range from 0.1 ml/min to 500 ml/min, 0.3 ml/min to 300 ml/min, 0.5 ml/min to 200 ml/min, 0.5 ml/min to 100 ml/min, from 1 ml/min to 80 ml/min, from 2 ml/min to 60 ml/min, or even from 2 ml/min to 50 ml/min.

In another advantageous aspect, the first addition stream and/or the optional third addition stream is incorporated into the reaction chamber of the multi-screw extruder at a flow speed in a range from 1 ml/min to 30 ml/min, from 2 ml/min to 25 ml/min, from 5 ml/min to 25 ml/min, from 5 ml/min to 20 ml/min, from 8 ml/min to 20 ml/min, or even from 10 ml/min to 20 ml/min.

In still another advantageous aspect, the second addition stream is incorporated into the reaction chamber of the multi-screw extruder at a flow speed in a range from 0.5 ml/min to 20 ml/min, from 1 ml/min to 20 ml/min, from 2 ml/min to 18 ml/min, from 3 ml/min to 15 ml/min, from 3 ml/min to 12 ml/min, or even from 4 ml/min to 10 ml/min.

The residence time of the reaction product stream comprising the compound comprising a (meth)acryloyl group in the reaction chamber of the multi-screw extruder for use herein is not particularly limited, thus making the process of the disclosure easy, simple and versatile. Suitable residence times for use herein will be easily identified by those skilled in the art, in the light of the present description.

According to a beneficial aspect of the process of the present disclosure, the residence time of the reaction product stream comprising the compound comprising a (meth)acryloyl group in the reaction chamber of the multi-screw extruder is in a range from 1 to 1200 seconds, from 5 to 900 seconds, from 10 to 600 seconds, from 10 to 300 seconds, from 10 to 250 seconds, from 10 to 200 seconds, from 10 to 180 seconds, from 15 to 160 seconds, from 15 to 140 seconds, from 15 to 120 seconds, from 15 to 100 seconds, from 15 to 80 seconds, from 15 to 60 seconds, from 15 to 50 seconds, or even from 15 to 40 seconds.

In another beneficial aspect of the process, the residence time of the reaction product stream comprising the compound comprising a (meth)acryloyl group in the reaction chamber of the multi-screw extruder no greater than 1200 seconds, no greater than 900 seconds, no greater than 600 seconds, no greater than 300 seconds, no greater than 250 seconds, no greater than 200, no greater than 150, no greater than 100 seconds, no greater than 80 seconds, or even no greater than 60 seconds.

The reactants, and in particular the first addition stream for use in the process according to the present disclosure may comprise an alcohol. Alcohols for use herein are not particularly limited. Suitable alcohols for use herein will be easily identified by those skilled in the art, in the light of the present description.

According to a typical aspect of the process, the alcohol for use herein comprises a monoalcohol having only one hydroxy group, wherein the monoalcohol is in particular selected from the group of aliphatic, aromatic, cyclic, linear, branched, unsaturated or heterocyclic monoalcohols.

According to an alternative typical aspect of the process, the alcohol for use herein comprises a poly alcohol having more than one hydroxy group, wherein the polyalcohol is in particular selected from the group of aliphatic, aromatic, cyclic, linear, branched, unsaturated or heterocyclic polyalcohols.

In one advantageous aspect, the alcohol for use herein is selected from the group of primary, secondary and tertiary alcohols.

In a beneficial aspect, the alcohol for use in the process of the present disclosure comprises a linear or branched alkyl group, having 1 to 60 carbon atoms, in particular from 4 to 40 carbon atoms. Examples include at least one of 1-butanol, 2-methylbutanol, 1-octanol, 2-octanol, isooctyl alcohol, 2-ethyl hexyl alcohol, 2-octyldodecanol, 2-hexyldecanol, 2-decyltetradecanol.

In another beneficial aspect, the alcohol comprises at least one ethylenically unsaturated group, such as in particular citronellol, nerol and geraniol.

In a further beneficial aspect, the alcohol is aromatic and/or comprises an aromatic group. Examples include phenol, 4-phenoxyphenol, 3-phenoxyphenol, benzylalcohol and benzophenone alcohols or substituted benzophenone alcohols, in particular 4-hydroxy benzophenone, 4-hydroxyethyl benzophenone, 2-hydroxy benzophenone, 3-hydroxy benzophenone, 4-chloro 4'-hydroxy benzophenone, 5-bromo 2-hydroxy benzophenone, 5-chloro 2-hydroxybenzophenone.

In a particularly beneficial aspect, the alcohol for use in the process of the present disclosure comprises at least one of 1-octanol, 2-octanol, citronellol, and 4-hydroxy benzophenone.

According to another typical aspect of the process, the alcohol for use herein has a weight average molecular weight of less than 1,000 g/mol, less than 900 g/mol, less than 800 g/mol, less than 700 g/mol, less than 600 g/mol, less than 550 g/mol, less than 500 g/mol, less than 450 g/mol, less than 400 g/mol, less than 350 g/mol, less than 300 g/mol, or even less than 250 g/mol.

The reactants, and in particular the first addition stream for use in the process according to the present disclosure may comprise a primary or secondary amine. Suitable primary or secondary amines for use herein will be easily identified by those skilled in the art, in the light of the present description.

According to a typical aspect of the process, the primary or secondary amine for use herein comprises a monoamine having only one amino group, wherein the monoamine is in particular selected from the group of aliphatic, aromatic, cyclic, linear, branched, unsaturated or heterocyclic monoamines.

According to an alternative typical aspect of the process, the primary or secondary amine or use herein comprises a polyamine having more than one amino group, wherein the polyamine is in particular selected from the group of aliphatic, aromatic, cyclic, linear, branched, unsaturated or heterocyclic polyamines.

In a beneficial aspect, the amine for use in the process of the present disclosure comprises at least one of linear or branched alkyl group, having 1 to 60 carbon atoms, in particular from 4 to 40 carbon atoms. Examples include butylamine, octylamine, aniline, benzylamine, octadecylamine, and any mixtures thereof.

According to another typical aspect of the process, the primary or secondary amine for use herein has an average weight molecular weight of less than 1,000 g/mol, less than 900 g/mol, less than 800 g/mol, less than 700 g/mol, less than 600 g/mol, less than 550 g/mol, less than 500 g/mol, less than 450 g/mol, less than 400 g/mol, less than 350 g/mol, less than 300 g/mol, or even less than 250 g/mol.

The appropriate amount of primary or secondary amine for use in the context of the process of the present disclosure, may be easily determined by those skilled in the art depending on the amount and starting reactants, and reagents which are selected.

According to a typical aspect of the process, the amount of amine for use herein, in particular in the first addition stream, is selected to be at least sufficient to react with the other reactants, in particular the (meth)acryloyl halide or the 3-halopropionyl halide.

Although less preferred, the amount of primary or secondary amine for use herein, in particular in the first addition stream, is selected to additionally neutralize substantially all or part of the hydrogen halide which is formed during the reaction process, and which may be at least temporarily comprised in the reaction product stream comprising the compound comprising a (meth)acryloyl group. According to that particular aspect, the addition of a base in the first or third addition stream becomes optional or the amount thereof can be reduced.

The reactants, and in particular the second addition stream for use in the process according to the present disclosure comprises a (meth)acryloyl halide or a 3-halopropionyl halide.

According to a typical aspect of the process, the (meth)acryloyl halide for use herein is (meth)acryloyl chloride and the 3-halopropionyl halide for use herein is 3-chloro-propionyl chloride.

In one particularly advantageous aspect, the (meth)acryloyl chloride for use in the process according to the disclosure is acryloyl chloride.

Acryloyl chloride and methacryloyl chloride are readily and commercially available for example from ABCR, Germany. Similarly, 3-chloropropionyl chloride is readily and commercially available for example from Sigma-Aldrich, Belgium.

The reagents, and in particular the first addition stream or the optional third addition stream for use in the process according to the present disclosure further comprises a base. Bases for use herein are not particularly limited. Any base commonly known in the art for similar chemical reactions may be used in the context of the present disclosure. Suitable bases for use herein will be easily identified by those skilled in the art, in the light of the present description.

According to an advantageous aspect of the process, the base for use herein comprises at least one of tertiary amines, in particular triethyl amine, trimethyl amine, methyldiethyl amine, pyridine, alkali metal hydroxide, and alkali earth metal hydroxide.

According to a preferred aspect of the process of the present disclosure, the base for use herein comprises triethyl amine. In another advantageous aspect, the base for use in the present process comprises potassium hydroxide, sodium hydroxide, or a mixture thereof. In another advantageous aspect, the base for use in the present process comprises mixtures of triethylamine and potassium hydroxide or sodium hydroxide.

The appropriate amount of base for use in the context of the process of the present disclosure, may be easily determined by those skilled in the art depending on the amount and the starting reactants which are selected.

According to one typical aspect of the process, where the (meth)acryloyl halide is incorporated through the second addition stream, the amount of base incorporated through the first addition stream or the optional third addition stream is selected to be at least sufficient to neutralize substantially all the hydrogen halide which is formed during the reaction process, and which may be at least temporarily comprised in the reaction product stream comprising the compound comprising a (meth)acryloyl group.

According to another typical aspect of the process, where 3-halopropionyl halide is incorporated through the second addition stream, the amount of base for use in the first (or optional third) addition stream, is selected to neutralize the hydrogen halide which is formed during the first reaction, where an intermediate 3-halopropionate ester or 3-halopropionamide is formed, and subsequently to dehydrohalogenate the intermediate 3-halopropionate ester or 3-halopropionamide to form the compound comprising the (meth)acryloyl group.

According to one advantageous aspect of the process of the present disclosure, the equivalent ratio of the alcohol to the base is 1 to at least 1; 1 to at least 1.5; 1 to at least 2; 1 to at least 2.5; 1 to at least 3; 1 to at least 3.5; 1 to at least 4; 1 to at least 4.5; or even 1 to at least 5.

According to another advantageous aspect of the process of the present disclosure, the equivalent ratio of the alcohol to the base is in a range between 1 to 1 and 1 to 5, between 1 to 1 and 1 to 4.5, between 1 to 1 and 1 to 4, between 1 to 1.5 and 1 to 4, between 1 to 1.5 and 1 to 3.5, between 1 to 2 and 1 to 4, or even between 1 to 2 and 1 to 3.

According to a preferred aspect of the process of the present disclosure, the equivalent ratio of the alcohol to the base is about 1 to 1, about 1 to 3, or even about 1 to 4.

According to one advantageous aspect of the process of the present disclosure, the equivalent ratio of the primary or secondary amine to the base is 1 to 0; 1 to at least 1; 1 to at least 1.5; 1 to at least 2; 1 to at least 2.5; 1 to at least 3; 1 to at least 3.5; 1 to at least 4; 1 to at least 4.5; or even 1 to at least 5.

According to another advantageous of the process of the present disclosure, the equivalent ratio of the primary or secondary amine to the base is 1 to 0, about 1 to 1, about 1 to 2, about 1 to 3, or about 1 to 4.

In another advantageous aspect of the process, the equivalent ratio of the alcohol or the primary or secondary amine to the (meth)acryloyl halide or 3-halopropionyl halide is 1 to at least 1; 1 to at least 1.02; 1 to at least 1.05; 1 to at least 1.1; 1 to at least 1.2; 1 to at least 1.3; 1 to at least 1.4; 1 to at least 1.5; 1 to at least 1.8; or even 1 to at least 2.

In still another advantageous aspect of the process, the equivalent ratio of the alcohol or the primary or secondary amine to the (meth)acryloyl halide or the 3-halopropionyl halide is in a range between 1 to 1 and 1 to 2, between 1 to 1 and 1 to 1.8, between 1 to 1 and 1 to 1.5, between 1 to 1 and 1 to 1.3, between 1 to 1 and 1 to 1.2, or even between 1 to 1 and 1 to 1.1.

In a preferred aspect of the process of the present disclosure, the equivalent ratio of the alcohol or the primary or secondary amine to the (meth)acryloyl halide or the 3-halopropionyl halide is about 1 to 1, or about 1 to 1.1.

In a further beneficial aspect of the process, the equivalent ratio of alcohol or amine to the (meth)acryloyl halide to the base is in a range between 1 to 1 to 1 and 1 to 1 to 5, between 1 to 1.05 to 1.05 and 1 to 1.05 to 4, between 1 to 1.1 to 1.1 and 1 to 1.1 to 4, between 1 to 1.2 to 1.2 and 1 to 1.2 to 4, or even between 1 to 1.5 to 1.5 and 1 to 1.5 to 4.

In still a further beneficial aspect of the process, the equivalent ratio of the alcohol or amine to the 3-halopropionyl halide to the base is in a range between 1 to 1 to 2 and 1 to 1 to 5, between 1 to 1.05 to 2.1 and 1 to 1.05 to 5, between 1 to 1.1 to 2.2 and 1 to 1.1 to 5, between 1 to 1.2 to 2.4 and 1 to 1.2 to 5, or even between 1 to 1.5 to 3 and 1 to 1.5 to 5.

The process of the present disclosure may be advantageously performed in a solventless environment. However, in a less preferred aspect, the reactants and reagents may comprise a solvent, as long as the solvent is unable to react with any of the reactants and reagents.

This additional solvent may be in particular advantageous in those situations where the reactants and reagents are not in a physical state suitable for them to be used in the first and/or the second and/or the optional third addition streams. This is in particular the case when the reactants and reagents of the first addition stream and/or the second addition stream and/or the optional third addition stream are neither liquid nor flowable/pumpable through conventional addition pumps (including high pressure pumps), even when subjected to a heating step. In other aspects, the use of an optional solvent may be advantageous to ensure optimized thermal management of the process in the reaction chamber of the multi-screw extruder or to reduce the viscosity of the reaction products formed.

Useful solvents for use herein are capable of dissolving the reactants, the reagents and the reaction products, but are inert in the sense that they do not react with the reactants and/or do not participate in the reaction. When suitable, the solvent may be used in any or all of the first, the second or optional third addition stream. The solvent used in the first addition stream may be the same or may be different from the solvent used in the second or optional third addition stream, depending on their respective reactivity with the reactants present in the particular addition streams. In one advantageous aspect, the at least one solvent is used in the first addition stream, together with the alcohol or primary or secondary amine and the base.

Suitable solvents for use herein include organic solvents and water.

According to a typical aspect of the process, the organic solvent for use herein is selected from the group consisting of polar solvents, in particular ethylacetate, 2-butanone, methyl isobutyl ketone, butylacetate, dimethylformamide, dimethylacetamide dichloromethane, and mixtures thereof, non-polar solvents, in particular cyclohexane, heptane and toluene and mixtures thereof.

In an advantageous aspect, the organic solvent may also be a diluent monomer. The diluent monomer does not participate in the reaction (i.e. is (meth)acryloyl halide free), but typically acts as a solvent to reduce the viscosity of the reaction mixture. After completion of the reaction, a ready to use mixture of (meth)acrylates or (meth)acrylamides, as made by the current process, and diluent monomer, is obtained that can be used in a further reaction step, including e.g. a polymerization reaction. Representative diluent monomers include compounds having an ethylenically unsaturated group. Preferred diluent monomers are (meth)acrylate monomers and include reactive diluents, in particular compounds of Formula (I):

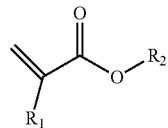

Formula (I)

wherein:
R$_1$ is H or C1 to C4 alkyl; and
R$_2$ is C1 to C12 alkyl optionally interrupted by one or more O atoms;
and any combinations or mixtures thereof.

In an exemplary aspect, the diluent monomer for use herein is selected from the group consisting of 2-ethylhexylacrylate, iso-octylacrylate, 3-propylheptylacrylate, 2-octylacrylate and 2-methylbutylacrylate, and mixtures thereof. In a particular advantageous aspect, the diluent monomer for use herein is selected from iso-octylacrylate or 2-ethylhexyl acrylate and mixtures thereof.

In another advantageous aspect, water can be used in the first addition stream, together with the alcohol or the primary or secondary amine and base, in order to provide a two-phase reaction system. Such a two-phase system allows for easy separation of the reaction products, that are present in the organic phase, from the salt, present in the water phase. It has surprisingly been found that the use of water in the first addition stream does not have a negative influence on the reaction yield, despite the water sensitivity of the reactants in the second addition stream, although the two streams are mixed in the reaction chamber.

According to one advantageous aspect of the process according to the present disclosure, the at least one solvent is selected from the group consisting of water, ethylacetate, 2-butanone, methyl isobutyl ketone, butylacetate, dimethylformamide, dimethylacetamide, dichloromethane, cyclohexane, heptane, toluene, ethylhexylacrylate, and compounds of Formula (I) in particular iso-octylacrylate, 2-octylacrylate, 2-methylbutylacrylate, and any mixtures thereof.

According to another advantageous aspect of the process, the at least one solvent for use herein is selected from the group consisting of water, dichloromethane, ethyl acetate, butyl acetate, methyl isobutyl ketone, and compounds of Formula (I) in particular iso-octylacrylate, 2-octylacrylate, 2-methylbutylacrylate, and any mixtures thereof.

According to still another advantageous aspect of the process, the at least one solvent is selected from the group consisting of water, ethylacetate, 2-butanone, methyl isobutyl ketone, butylacetate, dimethylformamide, dimethylacetamide, dichloromethane, cyclohexane, heptane, toluene, ethylhexylacrylate, compounds of Formula (I) in particular iso-octylacrylate, 2-octylacrylate, 2-methylbutylacrylate, and any mixtures thereof, and the at least one solvent is in particular incorporated as part of the first addition stream, together with the alcohol or the primary or secondary amine and the base.

In a typical aspect of the process, the step of incorporating the alcohol or the primary or secondary amine and the base into the reaction chamber of the multi-screw extruder comprises incorporating a solution of the alcohol or the primary or secondary amine in the at least one solvent into the reaction chamber of the multi-screw extruder.

In another typical aspect of the process, the step of incorporating the base into the reaction chamber of the multi-screw extruder comprises incorporating a solution of the base in the at least one solvent into the reaction chamber of the multi-screw extruder.

In one particular aspect of the present disclosure, the at least one solvent for use herein is selected from the group consisting of water, ethylacetate, 2-butanone, methyl isobutyl ketone, butylacetate, dichloromethane, cyclohexane, heptane, toluene, ethylhexylacrylate, compounds of Formula (I) in particular iso-octylacrylate, 2-octylacrylate, 2-methylbutylacrylate, and any mixtures thereof, and the at least one solvent is in particular incorporated as part of the second addition stream, together with the (meth)acryloyl halide or the 3-halopropionyl halide.

In another particular aspect of the process of the present disclosure, the step of incorporating the (meth)acryloyl halide or 3-halopropionyl halide into the reaction chamber of the multi-screw extruder comprises incorporating a solution of the (meth)acryloyl halide or the 3-halopropionyl halide in the at least one solvent into the reaction chamber of the multi-screw extruder.

According to a typical aspect of the process, the at least one solvent is incorporated into the reaction chamber of the multi-screw extruder in an amount sufficient to substantially dissolve the (meth)acryloyl halide or the 3-halopropionyl halide.

According to another typical aspect of the process, the at least one solvent is incorporated into the reaction chamber of the multi-screw extruder in an amount sufficient to reduce the viscosity of the reaction product.

According to still another typical aspect of the process, the at least one solvent is incorporated into the reaction chamber of the multi-screw extruder in an amount sufficient to produce a ready-to-use reaction mixture for further reactions, such as polymerization.

In one exemplary execution of the process, the first addition stream comprising the alcohol or the primary or secondary amine, the base and the optional solvent, is incorporated into the reaction chamber of the multi-screw extruder through the first addition port.

In another exemplary execution of the process, the second addition stream comprising the (meth)acryloyl halide or the 3-halopropionyl halide and the optional solvent, is incorporated into the reaction chamber of the multi-screw extruder through the second addition port.

In an alternative execution of the process, the reaction chamber of the multi-screw extruder further comprises a third addition port, and the base as well as the optional solvent are incorporated through the third addition port.

According to an alternative aspect of the present disclosure, the process for the manufacturing of a compound comprising a (meth)acryloyl group may be performed solventless.

In one typical aspect of the present process, the first addition stream and/or the second addition stream is free of solvents. In a particular aspect, both the first addition stream and the second addition stream are substantially free of solvents.

As will be apparent to those skilled in the art, the reaction product stream for use in the present process may comprise optional ingredients commonly known in the art for similar chemical reactions.

According to one advantageous aspect of the process of the disclosure, the first addition stream and/or the second addition stream and/or the optional third addition stream comprise suitable stabilizers or polymerization inhibitors. In particular, the first addition stream and/or the second addition stream and/or the optional third addition stream may comprise polymerization inhibitors specifically for the starting (meth)acryloyl halide or alternatively for the compound comprising a (meth)acryloyl group resulting from the process of the present disclosure.

In one beneficial aspect of the process, the stabilizers or polymerization inhibitors for use herein are selected from the group of phenothiazines and hydroquinones, in particular hydroquinone monomethyl ethers and hydroquinone methyl esters.

According to an advantageous aspect of the process of the present disclosure, the reaction product stream comprises the compound comprising a (meth)acryloyl group in an amount of at least 80 wt %, at least 85 wt %, at least 90 wt %, at least 95 wt %, or even at least 98 wt % based on the total weight of the compound comprising a (meth)acryloyl group, the alcohol or the primary or secondary amine, and organic by-products in the reaction product stream.

The weights of the various components of the product stream can be measured by any suitable means, for example, by gas chromatography or NMR spectroscopy. When gas chromatography is used, the compounds in the product stream can be identified by comparing their retention time to that of standards on the same column. The areas for the peaks can be calculated using standard software, or even manually, and then converted into concentration by using calibration curves. The calibration curves can be established by standard samples having known concentrations of the compounds. Other suitable means of determining the wt % of the various components of the product stream include, liquid chromatography, such as HPLC, and mass spectrometry.

According to another advantageous aspect of the process of the present disclosure, the conversion rate of the (meth)acryloyl halide or the 3-halopropionyl halide into the compound comprising a (meth)acryloyl group is of at least 80 mol %, at least 85 mol %, at least 90 mol %, at least 95 mol %, or even at least 98 mol % based on the molar equivalent of the (meth)acryloyl halide or the 3-halopropionyl halide, and when determined by $^1$H NMR spectroscopy.

In one advantageous aspect, the compound comprising a (meth)acryloyl group and resulting from the process of the present disclosure, has a weight average molecular weight of less than 1,000 g/mol, less than 900 g/mol, less than 800 g/mol, less than 700 g/mol, less than 600 g/mol, less than 550 g/mol, less than 500 g/mol, less than 450 g/mol, less than 400 g/mol, less than 350 g/mol, less than 300 g/mol, or even less than 250 g/mol.

In a preferred aspect of the disclosure, the compound comprising a (meth)acryloyl group comprises at least one of (meth)acrylic esters and (meth)acrylic amides, in particular (meth)acrylic esters.

In another preferred aspect of the process, the compound comprising a (meth)acryloyl group comprises (meth)acrylic esters selected from the group consisting of aliphatic or aromatic, linear or branched $C_1$-$C_{60}$ (meth)acrylic acid esters, $C_1$-$C_{24}$ (meth)acrylic acid esters, or even $C_1$-$C_{18}$ (meth)acrylic acid esters. More preferably, the (meth)acrylic esters are selected from the group consisting of methyl (meth)acrylate, ethyl (meth)acrylate, n-propyl (meth)acrylate, isopropyl (meth)acrylate, n-butyl acrylate, isobutyl acrylate, tert-butyl (meth)acrylate, n-pentyl (meth)acrylate, iso-pentyl (meth)acrylate, 2-methylbutyl (meth)acrylate, n-hexyl (meth)acrylate, iso-hexyl (meth)acrylate, cyclohexyl (meth)acrylate, phenyl (meth)acrylate, octyl (meth)acrylate, iso-octyl (meth)acrylate, 2-octyl(meth)acrylate, 2-ethylhexyl (meth)acrylate, decyl (meth)acrylate, undecyl (meth)acrylate, lauryl (meth)acrylate, tridecyl (meth)acrylate, tetradecyl (meth)acrylate, pentadecyl (meth)acrylate, hexadecyl (meth)acrylate, heptadecyl (meth)acrylate, 2-propylheptyl (meth)acrylate, stearyl (meth)acrylate, isobornyl (meth)acrylate, benzyl (meth)acrylate, nonyl (meth)acrylate, isophoryl (meth)acrylate, 2-hexyldecyl (meth)acrylate, 2-octyldodecyl (meth)acrylate, 2-decyltetradecyl (meth)acrylate, citronellyl acrylate, 4-acryloyl benzophenone, 4-methacryloyl benzophenone, dibutyl itaconate, di-2-ethylhexyl itaconate, dioctyl itaconate, monooctyl itaconate, mono 2-ethylhexyl itaconate, and any combinations or mixtures thereof.

In a particularly preferred aspect of the (meth)acrylic esters obtainable by the process of the present disclosure, are selected from the group consisting of 2-ethylhexyl (meth)acrylate, 2-propylheptyl (meth)acrylate, iso-octyl (meth)acrylate, 4-acryloyl benzophenone, and any combinations or mixtures thereof.

According to a typical aspect of the process of the disclosure, the reaction product stream may comprise one or more salts of the optional base and/or of the amine used in the first addition stream.

In one advantageous aspect of the process according to the disclosure, the reaction chamber of the multi-screw extruder is not cooled by cooling equipment.

This is a particularly surprising characteristic as the esterification or amidification reaction involving a (meth)acryloyl halide or a 3-halopropionyl halide is known to be highly exothermic, thus typically requiring external cooling to avoid potentially dangerous release of heat, unwanted side reactions, or both. Surprisingly, the process disclosed herein proceeds in high yields even when performed at room temperature and without necessarily using a cooling device for the reaction chamber of the multi-screw extruder.

According to one beneficial aspect of the present disclosure, the process as described herein may be performed as a continuous process.

In another aspect, the present disclosure relates to the use of a multi-screw extruder for the manufacturing of a compound comprising a (meth)acryloyl group and which has a weight average molecular weight of less than 1,000 g/mol.

According to an exemplary aspect of this use, the compound comprising an (meth)acryloyl group has a weight average molecular weight of less than 900 g/mol, less than 800 g/mol, less than 700 g/mol, less than 600 g/mol, less than 550 g/mol, less than 500 g/mol, less than 450 g/mol, less than 400 g/mol, less than 350 g/mol, less than 300 g/mol, or even less than 250 g/mol.

In one advantageous aspect, the compound comprising a (meth)acryloyl group comprises at least one of (meth)acrylic esters and (meth)acrylic amides, in particular (meth)acrylic esters.

In another advantageous aspect, the compound comprising a (meth)acryloyl group comprises (meth)acrylic esters selected from the group consisting of aliphatic or aromatic, linear or branched $C_1$-$C_{60}$ (meth)acrylic acid esters, $C_1$-$C_{24}$ (meth)acrylic acid esters, or even $C_1$-$C_{18}$ (meth)acrylic acid esters.

According to a preferred aspect of the present disclosure, the (meth)acrylic esters are selected from the group consisting of methyl (meth)acrylate, ethyl (meth)acrylate, n-propyl (meth)acrylate, isopropyl (meth)acrylate, n-butyl acrylate, isobutyl acrylate, tert-butyl (meth)acrylate, n-pentyl (meth)acrylate, iso-pentyl (meth)acrylate, 2-methylbutyl (meth)acrylate, n-hexyl (meth)acrylate, iso-hexyl (meth)acrylate, cyclohexyl (meth)acrylate, phenyl (meth)acrylate, octyl (meth)acrylate, iso-octyl (meth)acrylate, 2-octyl(meth)acrylate, 2-ethylhexyl (meth)acrylate, decyl (meth)acrylate, undecyl (meth)acrylate, lauryl (meth)acrylate, tridecyl (meth)acrylate, tetradecyl (meth)acrylate, pentadecyl (meth)acrylate, hexadecyl (meth)acrylate, heptadecyl (meth)acrylate, 2-propylheptyl (meth)acrylate, stearyl (meth)acrylate, isobornyl (meth)acrylate, benzyl (meth)acrylate, nonyl (meth)acrylate, isophoryl (meth)acrylate, 2-hexyldecyl (meth)acrylate, 2-octyldodecyl (meth)acrylate, 2-decyltetradecyl (meth)acrylate, citronellyl acrylate, 4-(meth)acryloyl benzophenone, dibutyl itaconate, di-2-ethylhexyl itaconate, dioctyl itaconate, monooctyl itaconate, mono 2-ethylhexyl itaconate, and any combinations or mixtures thereof.

All the particular and preferred aspects relating to in particular, the compound comprising a (meth)acryloyl group, the multi-screw extruder, the first and second addition stream, the alcohol, the primary or secondary amine, the (meth)acryloyl halide or the 3-halopropionyl halide, the base, the reaction product stream, and the optional solvent as described above in the context of the process for the manufacturing of a compound comprising a (meth)acryloyl group, are fully applicable to the description of the uses of the present disclosure, as described above.

Item 1 is a process for the manufacturing of a compound comprising a (meth)acryloyl group, wherein the process comprises the steps of
 a) providing a multi-screw extruder comprising a reaction chamber;
 b) providing reactants and reagents comprising:
  i. an alcohol or a primary or secondary amine;
  ii. a base; and
  ii. a (meth)acryloyl halide or a 3-halopropionyl halide; and
 c) incorporating the reactants and reagents into the reaction chamber of the multi-screw extruder, thereby forming a reaction product stream comprising the compound comprising a (meth)acryloyl group.

Item 2 is a process according to item 1, wherein the process further comprises the steps of
 a) providing a first addition stream comprising the alcohol or the primary or secondary amine and the base;
 b) providing a second addition stream comprising the (meth)acryloyl halide or the 3-halopropionyl halide; and c) incorporating the first addition stream and the second addition stream into the reaction chamber of the multi-screw extruder, thereby forming a reaction product stream comprising the compound comprising a (meth) acryloyl group.

Item 3 is a process according to item 1, wherein the process of the present disclosure comprises the steps of:
  a) providing a first addition stream comprising the alcohol or the primary or secondary amine;
  b) providing a second addition stream comprising (meth) acryloyl halide or the 3-halopropionyl halide;
  c) providing a third addition stream comprising the base; and
  d) incorporating the first addition stream, the second addition stream and the third addition stream into the reaction chamber of the multi-screw extruder, thereby forming a reaction product stream comprising the compound comprising a (meth)acryloyl group.

Item 4 is a process according to any of item 2 or 3, wherein the multi-screw extruder further comprises at least a first addition port, a second addition port, and optionally a third addition port, and the first addition stream is incorporated into the reaction chamber of the multi-screw extruder through the first addition port, the second addition stream is incorporated through the second addition port, and the optional third addition stream is incorporated through the optional third addition port.

Item 5 is process according to any of the preceding items, wherein the reactants and reagents, and in particular the first addition stream, the second addition stream, and the optional third addition stream are incorporated simultaneously into the reaction chamber of the multi-screw extruder.

Item 6 is a process according to any of items 1 to 4, wherein the reactants and reagents, and in particular the first addition stream, the second addition stream, and the optional third addition stream are incorporated into the reaction chamber of the multi-screw extruder in successive steps.

Item 7 is a process according to any of the preceding items, wherein the reactants and reagents, and in particular the first addition stream, the second addition stream, and the optional third addition stream are incorporated and combined, in particular through the movement of the multiple screws, in the reaction chamber of the multi-screw extruder, thereby forming a reaction product stream comprising the compound comprising a (meth)acryloyl group.

Item 8 is a process according to any of the preceding items, wherein the reactants and reagents, and in particular the first addition stream and the second addition stream are incorporated into the reaction chamber of the multi-screw extruder each at a flow speed in a range from 0.1 ml/min to 500 ml/min, 0.3 ml/min to 300 ml/min, 0.5 ml/min to 200 ml/min, 0.5 ml/min to 100 ml/min, from 1 ml/min to 80 ml/min, from 2 ml/min to 60 ml/min, or even from 2 ml/min to 50 ml/min.

Item 9 is a process according to any of the preceding items, wherein the first addition stream and/or the optional third addition stream is incorporated into the reaction chamber of the multi-screw extruder at a flow speed in a range from 1 ml/min to 30 ml/min, from 2 ml/min to 25 ml/min, from 5 ml/min to 25 ml/min, from 5 ml/min to 20 ml/min, from 8 ml/min to 20 ml/min, or even from 10 ml/min to 20 ml/min.

Item 10 is a process according to any of the preceding items, wherein the second addition stream is incorporated into the reaction chamber of the multi-screw extruder at a flow speed in a range from 0.5 ml/min to 20 ml/min, from 1 ml/min to 20 ml/min, from 2 ml/min to 18 ml/min, from 3 ml/min to 15 ml/min, from 3 ml/min to 12 ml/min, or even from 4 ml/min to 10 ml/min.

Item 11 is a process according to any of the preceding items, wherein the temperature of the reactants and reagents, and in particular the first addition stream, the second addition stream and the optional third addition stream are such that the reactants and reagents, and in particular the first addition stream, the second addition stream and the optional third addition stream are liquid prior to incorporation into the reaction chamber of the multi-screw extruder.

Item 12 is a process according to any of the preceding items, wherein the temperature of the reactants and reagents, and in particular the first addition stream, the second addition stream and the optional third addition stream is in a range from 0° C. to 120° C., from 0° C. to 100° C., from 0° C. to 80° C., from 0° C. to 70° C., from 5° C. to 60° C., from 10° C. to 55° C., from 15° C. to 45° C., from 20° C. to 35° C., or even from 20° C. to 25° C., prior to incorporation into the reaction chamber of the multi-screw extruder.

Item 13 is a process according to any of the preceding items, wherein the temperature of the reaction chamber is in a range from 0° C. to 120° C., from 0° C. to 100° C., from 0° C. to 80° C., from 0° C. to 70° C., from 5° C. to 60° C., from 10° C. to 60° C., from 15° C. to 60° C., from 15° C. to 55° C., from 15° C. to 50° C., from 15° C. to 40° C., or even from 20° C. to 30° C., after incorporation of the reactants and reagents, and in particular the first addition stream, the second addition stream and the optional third stream.

Item 14 is a process according to any of the preceding items, wherein the temperature of the reaction chamber is no greater than 120° C., no greater than 100° C., no greater than 80° C., no greater than 60° C., no greater than 50° C., no greater than 40° C., or even no greater than 30° C., after incorporation of the reactants and reagents, and in particular the first addition stream, the second addition stream and the optional third stream.

Item 15 is a process according to any of the preceding items, wherein the residence time of the reaction product stream comprising the compound comprising a (meth)acryloyl group in the reaction chamber of the multi-screw extruder is in a range from 1 to 1200 seconds, from 5 to 900 seconds, from 10 to 600 seconds, from 10 to 300 seconds, from 10 to 250 seconds, from 10 to 200 seconds, from 10 to 180 seconds, from 15 to 160 seconds, from 15 to 140 seconds, from 15 to 120 seconds, from 15 to 100 seconds, from 15 to 80 seconds, from 15 to 60 seconds, from 15 to 50 seconds, or even from 15 to 40 seconds.

Item 16 is a process according to any of the preceding items, wherein the residence time of the reaction product stream comprising the compound comprising a (meth)acryloyl group in the reaction chamber of the microflow reactor is no greater than 1200 seconds, no greater than 900 seconds, no greater than 600 seconds, no greater than 300 seconds, no greater than 250 seconds, no greater than 200, no greater than 150, no greater than 100 seconds, no greater than 80 seconds, or even no greater than 60 seconds.

Item 17 is a process according to any of the preceding items, wherein the multi-screw extruder is selected from the group of twin-screw extruders, planetary roller extruders, and ring extruders.

Item 18 is a process according to any of the preceding items, wherein the multi-screw extruder is operated at a screw speed in a range from 10 to 1200 rpm, from 20 to 1000 rpm, from 30 to 800 rpm, from 50 to 800 rpm, from 50 to 600 rpm, from 80 to 600 rpm, from 100 to 500 rpm, from 150 to 450 rpm, from 180 to 400 rpm, from 180 to 380 rpm, or even from 200 to 350 rpm.

Item 19 is a process according to any of the preceding items, wherein the multi-screw extruder is a co-rotating multi-screw extruder.

Item 20 is a process according to any of the preceding items, wherein the multi-screw extruder is a counter-rotating multi-screw extruder.

Item 21 is a process according to any of the preceding items, wherein the multi-screw extruder is a twin-screw extruder, in particular a co-rotating twin-screw extruder.

Item 22 is a process according to any of items 1 to 18, wherein the multi-screw extruder is a planetary roller extruder comprising in particular a center spindle and multiple planetary gear spindles with center spindle and planetary gear spindles featuring a screw like geometry.

Item 23 is a process according to any of the preceding items, wherein the alcohol comprises a monoalcohol having only one hydroxy group, wherein the monoalcohol is in particular selected from the group of aliphatic, aromatic, cyclic, linear, branched, unsaturated or heterocyclic monoalcohols.

Item 24 is a process according to any of the preceding items, wherein the alcohol comprises a poly alcohol having more than one hydroxy group, wherein the polyalcohol is in particular selected from the group of aliphatic, aromatic, cyclic, linear, branched, unsaturated or heterocyclic polyalcohols.

Item 25 is a process according to any of the preceding items, wherein the alcohol is selected from the group of primary, secondary and tertiary alcohols.

Item 26 is a process according to any of the preceding items, wherein the alcohol comprises at least one of 1-butanol, 2-methylbutanol, 1-octanol, 2-octanol, isooctyl alcohol, 2-ethyl hexyl alcohol, citronellol, nerol, geraniol, 2-octyldodecanol, 2-hexyldecanol, 2-decyltetradecanol, phenol, 4-phenoxyphenol, 3-phenoxyphenol, benzylalcohol and benzophenone alcohols or substituted benzophenone alcohols, in particular 4-hydroxy benzophenone, 4-hydroxyethyl benzophenone, 2-hydroxy benzophenone, 3-hydroxy benzophenone, 4-chloro 4'-hydroxy benzophenone, 5-bromo 2-hydroxy benzophenone, 5-chloro 2-hydroxybenzophenone.

Item 27 is a process according to any of the preceding items, wherein the alcohol comprises at least one of 1-octanol, 2-octanol, citronellol, and 4-hydroxy benzophenone.

Item 28 is a process according to any of the preceding items, wherein the alcohol has a weight average molecular weight of less than 1,000 g/mol, less than 900 g/mol, less than 800 g/mol, less than 700 g/mol, less than 600 g/mol, less than 550 g/mol, less than 500 g/mol, less than 450 g/mol, less than 400 g/mol, less than 350 g/mol, less than 300 g/mol, or even less than 250 g/mol.

Item 29 is a process according to any of the preceding items, wherein the primary or secondary amine comprises a monoamine having only one amino group, wherein the monoamine is in particular selected from the group of aliphatic, aromatic, cyclic, linear, branched, unsaturated or heterocyclic monoamines.

Item 30 is a process according to any of the preceding items, wherein the primary or secondary amine comprises a polyamine having more than one amino group, wherein the polyamine is in particular selected from the group of aliphatic, aromatic, cyclic, linear, branched, unsaturated or heterocyclic polyamines.

Item 31 is a process according to any of the preceding items, wherein the primary or secondary amine comprises at least one of butylamine, octylamine, aniline, benzylamine, octadecylamine, and any mixtures thereof.

Item 32 is a process according to any of the preceding items, wherein the primary or secondary amine has an average weight molecular weight of less than 1,000 g/mol, less than 900 g/mol, less than 800 g/mol, less than 700 g/mol, less than 600 g/mol, less than 550 g/mol, less than 500 g/mol, less than 450 g/mol, less than 400 g/mol, less than 350 g/mol, less than 300 g/mol, or even less than 250 g/mol.

Item 33 is a process according to any of the preceding items, wherein the base comprises at least one of tertiary amines, in particular triethyl amine, trimethyl amine, methyldiethyl amine, pyridine, alkali metal hydroxide, alkali earth metal hydroxide, and any mixtures thereof.

Item 34 is a process according to any of the preceding items, wherein the base comprises triethyl amine.

Item 35 is a process according to any of items 1 to 33, wherein the base comprises potassium hydroxide, sodium hydroxide, or a mixture thereof.

Item 36 is a process according to any of the preceding items, wherein the (meth)acryloyl halide or 3-halopropionyl halide is (meth)acryloyl halide, in particular (meth)acryloyl chloride.

Item 37 is a process according to item 36, wherein the (meth)acryloyl chloride is acryloyl chloride or methacryloyl chloride.

Item 38 is a process according to item 37, wherein the (meth)acryloyl chloride is acryloyl chloride.

Item 39 is a process according to item 37, wherein the (meth)acryloyl chloride is methacryloyl chloride.

Item 40 is a process according to any of items 1 to 35, wherein the (meth)acryloyl halide or 3-halopropionyl halide is 3-halopropionyl halide, in particular 3-chloropropionyl chloride.

Item 41 is a process according to any of the preceding items, wherein the equivalent ratio of the alcohol to the base is 1 to at least 1; 1 to at least 1.5; 1 to at least 2; 1 to at least 2.5; 1 to at least 3; 1 to at least 3.5; 1 to at least 4; 1 to at least 4.5; or even 1 to at least 5.

Item 42 is a process according to any of the preceding items, wherein the equivalent ratio of the alcohol to the base is in a range between 1 to 1 and 1 to 5, between 1 to 1 and 1 to 4.5, between 1 to 1 and 1 to 4, between 1 to 1.5 and 1 to 4, between 1 to 1.5 and 1 to 3.5, between 1 to 2 and 1 to 4, or even between 1 to 2 and 1 to 3.

Item 43 is a process according to any of the preceding items, wherein the equivalent ratio of the alcohol to the base is about 1 to 1, about 1 to 3, or even about 1 to 4.

Item 44 is a process according to any of the preceding items, wherein the equivalent ratio of the primary or secondary amine to the base is 1 to 0; 1 to at least 1; 1 to at least 1.5; 1 to at least 2; 1 to at least 2.5; 1 to at least 3; 1 to at least 3.5; 1 to at least 4; 1 to at least 4.5; 4 or even 1 to at least 5.

Item 45 is a process according to any of the preceding items, wherein the equivalent ratio of the primary or secondary amine to the base is 1 to 0, about 1 to 1, about 1 to 2, about 1 to 3, or even about 1 to 4.

Item 46 is a process according to any of the preceding items, wherein the equivalent ratio of the alcohol or the primary or secondary amine to the (meth)acryloyl halide or 3-halopropionyl halide is 1 to at least 1; 1 to at least 1.02; 1 to at least 1.05; 1 to at least 1.1; 1 to at least 1.2; 1 to at least 1.3; 1 to at least 1.4; 1 to at least 1.5; 1 to at least 1.8; or even 1 to at least 2.

Item 47 is a process according to any of the preceding items, wherein the equivalent ratio of the alcohol or the primary or secondary amine to the (meth)acryloyl halide or the 3-halopropionyl halide is in a range between 1 to 1 and 1 to 2, between 1 to 1 and 1 to 1.8, between 1 to 1 and 1 to 1.5, between 1 to 1 and 1 to 1.3, between 1 to 1 and 1 to 1.2, or even between 1 to 1 and 1 to 1.1.

Item 48 is a process according to any of the preceding items, wherein the equivalent ratio of the alcohol or the primary or secondary amine to the (meth)acryloyl halide or the 3-halopropionyl halide is about 1 to 1, or about 1 to 1.1.

Item 49 is a process to any of the preceding items, wherein the equivalent ratio of the alcohol or the primary or secondary amine to the (meth)acryloyl halide to the base is in a range between 1 to 1 to 1 and 1 to 1 to 5, between 1 to 1.05 to 1.05 and 1 to 1.05 to 4, between 1 to 1.1 to 1.1 and 1 to 1.1 to 4, between 1 to 1.2 to 1.2 and 1 to 1.2 to 4, or even between 1 to 1.5 to 1.5 and 1 to 1.5 to 4.

Item 50 is a process to any of the preceding items, wherein the equivalent ratio of the alcohol or the primary or secondary amine to the 3-halopropionyl halide to the base is in a range between 1 to 1 to 2 and 1 to 1 to 5, between 1 to 1.05 to 2.1 and 1 to 1.05 to 5, between 1 to 1.1 to 2.2 and 1 to 1.1 to 5, between 1 to 1.2 to 2.4 and 1 to 1.2 to 5, or even between 1 to 1.5 to 3 and i to 1.5 to 5.

Item 51 is a process according to any of the preceding items, wherein the reaction product stream comprises the compound comprising a (meth)acryloyl group in an amount of at least 80 wt %, at least 85 wt %, at least 90 wt %, at least 95 wt %, or even at least 98 wt % based on the total weight of the compound comprising a (meth)acryloyl group, the alcohol or the primary or secondary amine, and organic by-products in the reaction product stream, as determined by gas chromatography.

Item 52 is a process according to any of the preceding items, wherein the conversion rate of the (meth)acryloyl halide or the 3-halopropionyl halide into the compound comprising a (meth)acryloyl group is of at least 80 mol %, at least 85 mol %, at least 90 mol %, at least 95 mol %, or even at least 98 mol % based on the molar equivalent of the (meth)acryloyl halide or the 3-halopropionyl halide, and when determined by $^1$H NMR spectroscopy.

Item 53 is a process according to any of the preceding items, wherein the compound comprising a (meth)acryloyl group has a weight average molecular weight of less than 1,000 g/mol, less than 900 g/mol, less than 800 g/mol, less than 700 g/mol, less than 600 g/mol, less than 550 g/mol, less than 500 g/mol, less than 450 g/mol, less than 400 g/mol, less than 350 g/mol, less than 300 g/mol, or even less than 250 g/mol.

Item 54 is a process according to any of the preceding items, wherein the compound comprising a (meth)acryloyl group comprises at least one of (meth)acrylic esters and (meth)acrylic amides, in particular (meth)acrylic esters.

Item 55 is a process according to any of the preceding items, wherein the compound comprising a (meth)acryloyl group comprises (meth)acrylic esters selected from the group consisting of aliphatic or aromatic, linear or branched $C_1$-$C_{60}$ (meth)acrylic acid esters, $C_1$-$C_{24}$ (meth)acrylic acid esters, or even $C_1$-$C_{18}$ (meth)acrylic acid esters.

Item 56 is a process according to item 52, wherein the (meth)acrylic esters are selected from the group consisting of methyl (meth)acrylate, ethyl (meth)acrylate, n-propyl (meth)acrylate, isopropyl (meth)acrylate, n-butyl acrylate, isobutyl acrylate, tert-butyl (meth)acrylate, n-pentyl (meth) acrylate, iso-pentyl (meth)acrylate, 2-methylbutyl (meth) acrylate, n-hexyl (meth)acrylate, iso-hexyl (meth)acrylate, cyclohexyl (meth)acrylate, phenyl (meth)acrylate, octyl (meth)acrylate, iso-octyl (meth)acrylate, 2-octyl(meth)acrylate, 2-ethylhexyl (meth)acrylate, decyl (meth)acrylate, undecyl (meth)acrylate, lauryl (meth)acrylate, tridecyl (meth)acrylate, tetradecyl (meth)acrylate, pentadecyl (meth) acrylate, hexadecyl (meth)acrylate, heptadecyl (meth)acrylate, 2-propylheptyl (meth)acrylate, stearyl (meth)acrylate, isobornyl (meth)acrylate, benzyl (meth)acrylate, nonyl (meth)acrylate, isophoryl (meth)acrylate, 2-hexyldecyl (meth)acrylate, 2-octyldodecyl (meth)acrylate, 2-decyltetradecyl (meth)acrylate, 4-(meth)acryloyl benzophenone, dibutyl itaconate, di-2-ethylhexyl itaconate, dioctyl itaconate, monooctyl itaconate, mono 2-ethylhexyl itaconate, and any combinations or mixtures thereof.

Item 57 is a process according to item 56, wherein the (meth)acrylic esters are selected from the group consisting of 2-ethylhexyl (meth)acrylate, 2-propylheptyl (meth)acrylate, iso-octyl (meth)acrylate, 4-(meth)acryloyl benzophenone, and any combinations or mixtures thereof.

Item 58 is a process according to any of the preceding items, wherein the reaction product stream comprises one or more salts of the base.

Item 59 is a process according to any of the preceding items, which further comprises the step of incorporating at least one solvent into the reaction chamber of the multi-screw extruder.

Item 60 is a process according to claim 59, wherein the solvent is selected from the group consisting of water; polar solvents, in particular ethylacetate, 2-butanone, methyl isobutyl ketone, butylacetate, dimethylformamide, dimethylacetamide and dichloromethane; non-polar solvents, in particular cyclohexane, heptane and toluene; diluent monomers, in particular compounds of Formula (I):

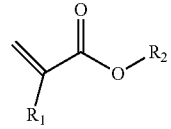

Formula (I)

wherein:
$R_1$ is H or C1 to C4 alkyl; and
$R_2$ is C1 to C12 alkyl optionally interrupted by one or more O atoms;
and any combinations or mixtures thereof.

Item 61 is a process according to claim 60, wherein the diluent monomer is selected from the group consisting of 2-ethylhexylacrylate, iso-octylacrylate, 3-propylheptylacrylate, 2-octylacrylate and 2-methylbutylacrylate.

Item 62 is a process according to any of item 60 or 61, wherein the at least one solvent is selected from the group consisting of water, ethylacetate, 2-butanone, methyl isobutyl ketone, butylacetate, dimethylformamide, dimethylacetamide, dichloromethane, cyclohexane, heptane, toluene, ethylhexylacrylate, and compounds of Formula (I) in particular iso-octylacrylate, 2-octylacrylate, 2-methylbutylacrylate, and any mixtures thereof.

Item 63 is a process according to any of items 60 to 62, wherein the at least one solvent is selected from the group consisting of water, dichloromethane, ethyl acetate, butyl acetate, 2-butanone, methyl butyl ketone, and compounds of Formula (I) in particular iso-octylacrylate, 2-octylacrylate, 2-methylbutylacrylate, and any mixtures thereof.

Item 64 is a process according to any of items 60 to 63, wherein the at least one solvent is selected from the group consisting of water, ethylacetate, 2-butanone, methyl isobutyl ketone, butylacetate, dimethylformamide, dimethylacetamide, dichloromethane, cyclohexane, heptane, toluene, ethylhexylacrylate, compounds of Formula (I) in particular iso-octylacrylate, 2-ethylhexylacrylate, 2-octylacrylate, 2-methylbutylacrylate, and any mixtures thereof, and wherein the at least one solvent is incorporated as part of the first addition stream, together with the alcohol or amine and the optional base.

Item 65 is a process according to item 64, wherein the step of incorporating the alcohol or the primary or secondary amine into the reaction chamber of the multi-screw extruder comprises incorporating a solution of the alcohol or the primary or secondary amine in the at least one solvent into the reaction chamber of the multi-screw extruder.

Item 66 is a process according to item 64, wherein the step of incorporating the base into the reaction chamber of the multi-screw extruder comprises incorporating a solution of the base in the at least one solvent into the reaction chamber of the multi-screw extruder.

Item 67 is a process according to any of items 60 to 63, wherein the at least one solvent is selected from the group consisting of water, ethylacetate, 2-butanone, methyl isobutyl ketone, butylacetate, dichloromethane, cyclohexane, heptane, toluene, ethylhexylacrylate, compounds of Formula (I) in particular iso-octylacrylate, 2-octylacrylate, 2-methylbutylacrylate, and any mixtures thereof, and wherein the at least one solvent is incorporated as part of the second addition stream, together with the (meth)acryloyl halide or the 3-halopropionyl halide.

Item 68 is a process according to item 67, wherein the step of incorporating the (meth)acryloyl halide or 3-halopropionyl halide into the reaction chamber of the multi-screw extruder comprises incorporating a solution of the incorporating the (meth)acryloyl halide or the 3-halopropionyl halide in the at least one solvent into the reaction chamber of the multi-screw extruder.

Item 69 is a process according to any of items 60 to 68, wherein the at least one solvent is incorporated into the reaction chamber of the multi-screw extruder in an amount sufficient to substantially dissolve the (meth)acryloyl halide or the 3-halopropionyl halide.

Item 70 is a process according to any of items 1 to 59, wherein the first addition stream and/or the second addition stream and/or the optional third addition stream is free of solvents.

Item 71 is a process according to any preceding items, where the first addition stream and/or the second addition stream and/or the optional third addition stream comprise stabilizers or polymerization inhibitors for the (meth)acryloyl halide or the compound comprising a (meth)acryloyl group.

Item 72 is a process according to item 71, wherein the stabilizers or polymerization inhibitors are selected from the group of phenothiazines and hydroquinones, in particular hydroquinone monomethyl ethers and hydroquinone methyl esters.

Item 73 is a process according to any of the preceding items, wherein the first addition stream comprising the alcohol or the primary or secondary amine, the base and the optional solvent, is incorporated into the reaction chamber of the multi-screw extruder through the first addition port.

Item 74 is a process according to any of the preceding items, wherein the second addition stream comprising the (meth)acryloyl halide or the 3-halopropionyl halide and the optional solvent, is incorporated into the reaction chamber of the multi-screw extruder through the second addition port.

Item 75 is a process according to any of the preceding items 1 to 74, wherein the reaction chamber of the multi-screw extruder further comprises a third addition port, and wherein the optional solvent is incorporated through the third addition port.

Item 76 is a process according to any of the preceding items, wherein the reaction chamber of the multi-screw extruder is not cooled by cooling equipment.

Item 77 is a process according to any of the preceding items, which is a continuous process.

Item 78 is the use of a multi-screw extruder for the manufacturing of a compound comprising an (meth)acryloyl group which has a weight average molecular weight of less than 1,000 g/mol.

Item 79 is the use according to item 78, wherein the compound comprising an (meth)acryloyl group has a weight average molecular weight of less than 900 g/mol, less than 800 g/mol, less than 700 g/mol, less than 600 g/mol, less than 550 g/mol, less than 500 g/mol, less than 450 g/mol, less than 400 g/mol, less than 350 g/mol, less than 300 g/mol, or even less than 250 g/mol.

Item 80 is the use according to any of item 78 or 79, wherein the compound comprising a (meth)acryloyl group comprises at least one of (meth)acrylic esters and (meth)acrylic amides, in particular (meth)acrylic esters.

Item 81 is the use according to any of items 78 to 80, wherein the compound comprising a (meth)acryloyl group comprises (meth)acrylic esters selected from the group consisting of aliphatic or aromatic, linear or branched $C_1$-$C_{60}$ (meth)acrylic acid esters, $C_1$-$C_{24}$ (meth)acrylic acid esters, or even $C_1$-$C_{18}$ (meth)acrylic acid esters.

Item 82 is the use according to item 81, wherein the (meth)acrylic esters are selected from the group consisting of methyl (meth)acrylate, ethyl (meth)acrylate, n-propyl (meth)acrylate, isopropyl (meth)acrylate, n-butyl acrylate, isobutyl acrylate, tert-butyl (meth)acrylate, n-pentyl (meth)acrylate, iso-pentyl (meth)acrylate, 2-methylbutyl (meth)acrylate, n-hexyl (meth)acrylate, iso-hexyl (meth)acrylate, cyclohexyl (meth)acrylate, phenyl (meth)acrylate, octyl (meth)acrylate, iso-octyl (meth)acrylate, 2-octyl(meth)acrylate, 2-ethylhexyl (meth)acrylate, decyl (meth)acrylate, undecyl (meth)acrylate, lauryl (meth)acrylate, tridecyl (meth)acrylate, tetradecyl (meth)acrylate, pentadecyl (meth)acrylate, hexadecyl (meth)acrylate, heptadecyl (meth)acrylate, 2-propylheptyl (meth)acrylate, stearyl (meth)acrylate, isobornyl (meth)acrylate, benzyl (meth)acrylate, nonyl (meth)acrylate, isophoryl (meth)acrylate, 2-hexyldecyl (meth)acrylate, 2-octyldodecyl (meth)acrylate, 2-decyltetradecyl (meth)acrylate, 4-(meth)acryloyl benzophenone, dibutyl itaconate, di-2-ethylhexyl itaconate, dioctyl itaconate, monooctyl itaconate, mono 2-ethylhexyl itaconate, and any combinations or mixtures thereof.

EXAMPLES

The present disclosure is further illustrated by the following examples. These examples are merely for illustrative purposes only and are not meant to be limiting on the scope of the appended claims.

The following abbreviations are used in this section: NMR=nuclear magnetic resonance, ml=milliliters, rpm=rounds per minute, min=minutes, g=grams, mm=millimeters, ppm=parts per million. Abbreviations of materials used in this section, as well as descriptions of the materials, are provided in Table 1.

TABLE 1

| Material | Description |
| --- | --- |
| BP | 4-hydroxybenzophenone, available from Aldrich, Belgium |
| TEA | triethylamine, available from Aldrich, Belgium |
| Water | de-ionized water |
| ACL | acryloylchloride, available from ABCR, Germany |
| IOA | isooctylacrylate, available from Aldrich, Belgium |
| CiOH | citronellol, available from Aldrich, Belgium |
| OOH | 2-octanol, available from Aldrich, Belgium |
| EtOAc | ethyl acetate, available from Aldrich, Belgium |
| NaOH | sodium hydroxide, available from Aldrich, Belgium |

Test Methods and Characterization:

Equivalent Ratio

The term "Equivalent Ratio" is used throughout this section to mean the ratio or ratios of indicated reactants incorporated into the reaction chamber of the twin-screw extruder.

% Composition

The term "% Composition" is used throughout this section to mean the percent, by weight, of the specified compound in the reaction product stream, with respect to the combination of all components identified in the reaction product stream by either gas chromatography (GC) or NMR, excluding solvent. In some examples where a liquid two-phase system is obtained as a reaction product stream, the "% Composition" refers to weight % of the specified compound in the organic portion of the reaction product stream. The concentrations are determined either by GC or NMR, as described below, under "Characterization."

Characterization

GC: In some examples, the concentration of the components in the reaction product stream from the twin-screw extruder is determined using a gas chromatograph (GC) available under the trade designation "6890N" from Agilent Technologies, USA, using a flame ionization detector. The column used is a 95% polydimethylsiloxane/5% polydiphenylsiloxane, 30 m length, 0.32 mm diameter, 0.25 μm film thickness, available under the trade designation "HP-5" from Agilent Technologies, USA. Hydrogen is used as the carrier gas. Areas of peaks for compounds identified by retention time is converted to concentration values using calibration curves established for known concentrations of standards of the compounds.

NMR: Analysis by NMR is made using a Bruker Avance 300 Digital NMR spectrometer equipped with Bruker 5 mm BBFO 300 MHz Z-gradient high resolution-ATM probe. The samples are placed in NMR tubes available under the trade designation "WG-5M-ECONOMY" from Aldrich, Belgium. TMS (tetramethylsilane, available from Aldrich, Belgium) is added as a zero ppm reference. Proton NMR spectra are acquired using the following parameters:

Pulse Angle: 30°
Number of Scans: 128
Acquisition Time: 5.3 s
Relaxation time: 2.0 s Except where noted, NMR confirmed the identity of the desired products.

Equipment Employed:

The experiments and reactions are performed using a twin-screw extruder available under the trade designation PROCESS 11 PARALLEL TWIN-SCREW EXTRUDER, from Thermo Fischer Scientific, Germany. The twin-screw extruder is equipped with at least two addition ports. Two ultra-compact high-pressure pumps acting as dosing units and available under the trade designation AZURA P 4.1S, from Knauer, Germany, are connected to two containers containing the reagents and deliver at least two reactant addition streams through PFA tubing with an inner diameter of 0.5 mm, available under the trade designation "IDEX 1512L" from Achrom, Belgium, to at least two addition ports of the twin-screw extruder using connectors available from Achrom. The at least two reactant addition streams are incorporated and combined into the reaction chamber of the multi-screw extruder, where a reaction product stream is formed. The reaction product stream exits the multi-screw extruder through a product port and in some examples, flows through PFA tubing with an inner diameter of 1 mm, connected to the product port using connectors available from Achrom, Belgium, into a collection vessel. In some other examples, the reaction product stream directly exits the multi-screw extruder through a product port.

EXAMPLES

Example 1

For Ex.1, the following procedure is carried out using the twin-screw extruder at ambient temperature. A blend of 2-octanol OOH (13 grams) and TEA (50 grams) is prepared as a first addition stream (Stream I) and incorporated through a first addition port of the extruder at a flow speed of 15 ml/min. Pure ACL is incorporated as a second addition stream (Stream II) through a second addition port of the extruder at a flow speed of 5 ml/min. The equivalent ratios of OOH:ACL:TEA incorporated into the reaction chamber are 1:1.1:2.9. The screw speed of the extruder is set to 200 rpm. The resulting reaction product stream is a viscous material. The concentration of 2-octylacrylate is determined by GC as detailed in Table 2.

TABLE 2

| Amounts of OOH and TEA are indicated in grams | | | | |
| --- | --- | --- | --- | --- |
| | Stream I | Stream II | Equivalent ratios | % |
| Example | OOH TEA | ACL | (OOH:ACL:TEA) | 2-octylacrylate |
| Ex. 1 | 13   50 | Pure | 1:1.1:2.9 | 99.5 |

As can be seen from the result in Table 2 above, 2-octyl acrylate is obtained in very high yield, from a solventless reaction, in the twin-screw extruder, with a first addition stream (Stream I) comprising 2-octylalcohol and triethylamine, and a second addition stream (Stream II) comprising acryloyl chloride.

Examples 2 to 5

For Ex.2 to Ex.5, the following general procedure is carried out using the twin-screw extruder at ambient temperature. A blend of BP (100 g), TEA (50 g), NaOH (20 g) and water (147 g) is prepared as a first addition stream (Stream I) and incorporated through a first addition port of the extruder at the flow speed in Table 3. A blend of ACL (40 g) and IOA (80 g) is prepared and incorporated as a second addition stream (Stream II) through a second addition port at the flow speed in Table 3. The equivalent ratios of BP:ACL:TEA:NaOH incorporated into the reaction chamber are 1:1.1:2.9:1. The various screw speeds used in examples 2 to 5 are specified in Table 3. The resulting reaction product streams are liquid two-phase systems. The organic phase comprising the BP-acrylate (referring to 4-acryloylbenzophenone or ABP) is separated from the aqueous phase by using a separatory funnel. The concentration of 4-acryloylbenzophenone (ABP) in the organic phase is determined by NMR as detailed in Table 3.

TABLE 3

Stream I and Stream II flow speeds are indicated in ml/min
Screw speeds are indicated in rpm

| Example | Stream I Flow Speed | Stream II Flow Speed | Screw speed | Equivalent ratio (BP:ACL:TEA:NaOH) | % ABP |
|---|---|---|---|---|---|
| Ex. 2 | 14 | 9 | 350 | 1:1.1:2.9:1 | 84 |
| Ex. 3 | 14 | 9 | 200 | 1:1.1:2.9:1 | 87 |
| Ex. 4 | 14 | 7 | 200 | 1:1.1:2.9:1 | 95 |
| Ex. 5 | 18 | 12 | 350 | 1:1.1:2.9:1 | 100 |

As can be seen from the results in Table 3, 4-acryloylbenzophenone is surprisingly obtained in high yield from reaction in a twin-screw reactor, with a first addition stream (Stream I), comprising 4-hydroxybenzophenone, triethylamine, sodiumhydroxide and water, and a second addition stream (Stream II) comprising acryloylchloride. This surprising high yield is obtained despite the presence of water in Stream I.

Example 6

For Ex.6, the following procedure is carried out using the twin-screw extruder at ambient temperature. A blend of CiOH (15.6 g) and TEA (50 g) is prepared as a first addition stream (Stream I) and incorporated through a first addition port of the extruder at a flow speed of 7.5 ml/min. Pure ACL is incorporated as a second addition stream (Stream II) through a second addition port of the extruder at a flow speed of 4.5 ml/min. The equivalent ratios of CiOH:ACL:TEA incorporated into the reaction chamber are 1:1.1:2.9. The screw speed of the extruder is set to 200 rpm. The resulting reaction product stream is a solid material. The concentration of citronellyl acrylate is determined by NMR as detailed in Table 4.

TABLE 4

Amounts of CiOH and TEA are indicated in grams

| Example | Stream I CiOH | TEA | Stream II ACL | Equivalent ratios (CiOH:ACL:TEA) | % citronellylacrylate |
|---|---|---|---|---|---|
| Ex. 6 | 15.6 | 50 | Pure | 1:1.1:2.9 | 99.5 |

As can be seen from the result in Table 4, citronellyl acrylate is obtained in very high yield, from a solventless reaction, in the twin-screw extruder, starting from a first addition stream (Stream I), comprising citronellol and triethylamine, and a second addition stream (Stream II) comprising acryloylchloride.

The invention claimed is:
1. A process for the manufacturing of a compound comprising a (meth)acryloyl group, wherein the process comprises the steps of:
   a) providing a multi-screw extruder comprising a reaction chamber;
   b) providing reactants and reagents comprising:
      i. an alcohol or a primary or secondary amine;
      ii. a base; and
      iii. a (meth)acryloyl halide or a 3-halopropionyl halide; and
   c) incorporating the reactants and reagents into the reaction chamber of the multi-screw extruder, thereby forming a reaction product stream comprising the compound comprising a (meth)acryloyl group.

2. A process according to claim 1, wherein the multi-screw extruder is selected from the group of twin-screw extruders, planetary roller extruders, and ring extruders.

3. A process according to claim 1, wherein the multi-screw extruder is a co-rotating multi-screw extruder.

4. A process according to claim 1, wherein the temperature of the reaction chamber is in a range from 0° C. to 120° C., from 0° C. to 100° C., from 0° C. to 80° C., from 0° C. to 70° C., from 5° C. to 60° C., from 10° C. to 60° C., from 15° C. to 60° C., from 15° C. to 55° C., from 15° C. to 50° C., from 15° C. to 40° C., or from 20° C. to 30° C., after incorporation of the reactants and reagents.

5. A process according to claim 1, wherein the alcohol comprises a monoalcohol having only one hydroxy group, wherein the monoalcohol is selected from the group of aliphatic, aromatic, cyclic, linear, branched, saturated, unsaturated or heterocyclic monoalcohols.

6. A process according to claim 1, wherein the alcohol is selected from the group of primary, secondary and tertiary alcohols.

7. A process according to claim 1, wherein the primary or secondary amine comprises a monoamine having only one amino group, wherein the monoamine is selected from the group of aliphatic, aromatic, cyclic, linear, branched, saturated, unsaturated or heterocyclic monoamines.

8. A process according to claim 1, wherein the base comprises at least one of tertiary amines, triethyl amine, trimethyl amine, methyldiethyl amine, pyridine, alkali metal hydroxide, or alkali earth metal hydroxide, or any mixtures thereof.

9. A process according to claim 1, wherein the (meth) acryloyl halide or 3-halopropionyl halide is (meth)acryloyl halide, methacryloyl chloride or acryloyl chloride.

10. A process according to claim 1, wherein the (meth) acryloyl halide or 3-halopropionyl halide is 3-halopropionyl halide or 3-chloropropionyl chloride.

11. A process according to claim 1, wherein the equivalent ratio of the alcohol or the primary or secondary amine to the (meth)acryloyl halide or 3-halopropionyl halide is 1 to at least 1; 1 to at least 1.02; 1 to at least 1.05; 1 to at least 1.1; 1 to at least 1.2; 1 to at least 1.3; 1 to at least 1.4; 1 to at least 1.5; 1 to at least 1.8; or 1 to at least 2.

12. A process according to claim 1, wherein the compound comprising a (meth)acryloyl group comprises at least one of (meth)acrylic esters and (meth)acrylic amides.

13. A process according to claim 1, which further comprises the step of incorporating at least one solvent into the reaction chamber of the multi-screw extruder.

14. A process according to claim 13, wherein the solvent is selected from the group consisting of water, polar solvents, ethyl acetate, 2-butanone, methyl isobutyl ketone, butyl acetate, dimethylformamide, dimethylacetamide, dichloromethane, non-polar solvents, cyclohexane, heptane, toluene, diluent monomers, compounds of Formula (I):.

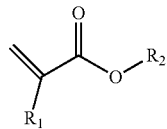
Formula (I)
wherein:
$R_1$ is H or $C_1$ to C4 alkyl; and
$R_2$ is C1 to C12 alkyl optionally interrupted by one or more O atoms;
and any combinations or mixtures thereof.
15. A process according to claim 1 wherein the compound comprising a (meth)acryloyl group has a weight average molecular weight of less than 1,000 g/mol.
\* \* \* \* \*